United States Patent [19]

Guillou et al.

[11] Patent Number: Plant 7,373

[45] Date of Patent: Oct. 30, 1990

[54] VARIETY OF GERANIUM NAMED CAMILLE

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 360,012

[22] Filed: Jun. 1, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenheim & Webb

[57] ABSTRACT

A new and distinct Geranium variety adds to the current Ivy Geranium class not only with a new color but with a stronger ability to tolerate high temperatures. The medium green foliage with its upright yet cascading habit is accented with light orchid blossoms forming an eye pleasing hanging basket.

1 Drawing Sheet

BACKGROUND OF THE NEW PLANT

The present invention comprises a new and distinct cultivar of *Pelargonium*×*peltatum* known by the varietal name Camille (Oglevee Ltd. No. 7035, French No. 91 Guisorel). The new variety was discovered in a selective breeding program by Messrs. Jacques, Maurice and Bernard Guillou. The new variety is a selection from a crossing of No. 553×No. 85. The new cultivar has a more compact foliage than its parentage.

The new cultivar was discovered in 1986 at 55 rue Godard, 35400 Saint-Malo, France, was first asexually reproduced by cuttings during 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., using full light, 60° F. night temperature, 68° F. day temperature, 71° F. vent temperature, and grown in a soilless media with constant fertilizer of 200-250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988. Three 10 cm pots were potted into a 26 cm hanging basket and maintained until Mar. 4, 1989 when the color readings were taken. The plant histories were taken of plants blossomed under full light in a greenhouse and color readings were taken indoors under 200-220 foot candles of cool white fluorescent light. Color references are primarily to the R.H.S. Colour Chart of the Royal Horticultural Society of London.

THE PLANT

Classification:

*Botanical.*—*Pelargonium*×*peltatum.*

*Commercial.*—Ivy Geranium (#7035) Camille.

Form: Cascading mound habit.

Height: 26 cm above media surface.

Growth: Free branching, upright growth with some cascading side growth, free and early flowering.

Strength: Holds an upright mound shape while allowing outer branches to cascade over the sides of the pot.

Foliage: Stalked leaf attachment; zone present but very faint.

Leaves:

*Size.*—5.5-7.5, fully expanded leaf.

*Shape.*—Reniform, cordate base.

*Margin.*—Pedately lobed.

*Texture.*—Dull; non-reflective; slightly pubescent.

*Color.*—Top: Green group 137B; Bottom: Green group 137C.

*Ribs and veins.*—Palmate venation; Color: Yellow-green group 146C.

Petioles: 3-4.5 cm in length.

*Color.*—Yellow-green group 146B.

Stem:

*Color.*—Yellow-green group 146B.

*Internodes.*—1.5-6 cm in length.

THE BUD

Shape: Elliptical cluster; 5-9 buds per umbel peduncle is bent allowing umbel to droop until maturity when the umbel and peduncle stand straight.

Size: 2-2.5 cm across.

INFLORESCENCE

Blooming habit: Continuous; upright.

Size: 7-9 cm across when fully opened.

Borne: Florets on pedicel; pedicel on peduncle; umbel 4-6 cm above foliage canopy.

Florets:

*Form.*—Flat to slightly cupped.

*Color.*—Top: Red-purple group 68B. Bottom: Red-purple group 68D. Venation: Red-purple group 61B.

*Petals.*—5–7 in number, not united, separate; margin entire.

*Floret Size.*—4–4.5 cm across.

*Texture and appearance.*—Smooth; single floret containing 5–7 petals; appearance from a distance is orchid with 2–3 upper petals having burgundy markings.

Petaloids:

*Quantity.*—None present.

Pedicel: 3.5–4 cm in length.

*Color.*—Top: Greyed-purple group 187B. Bottom: Yellow-green group 146B. The color of the pedicel is quite unique; if viewing from the top, the color is greyed-purple or if viewed from the bottom the color is yellow-green; a distinct color division is noticed.

Peduncle: 6.5–9.5 cm in length.

*Color.*—Yellow-green group 146A.

Disease resistance; Not known.

Lasting quality: This variety is very heat tolerant.

REPRODUCTIVE ORGANS

Stamens:

*Anthers.*—2–3 mm in length.

*Filaments.*—8–10 mm in length; white irregular shape.

*Pollen.*—Golden brown.

Pistils:

*Number.*—One; 5 or 6 parted stigma.

*Length.*—11–12 mm.

*Stigma.*—5 or 6 parted.

*Style.*—5–6 mm in length; white to very pale pink.

Ovaries: Superior; pubescent; pale green; 5–6 mm in length, 2–3 mm across.

Fruit: None observed.

GENERAL CHARACTERISTICS

This variety is new and distinct in that it adds to the current Ivy Geranium class not only with a new color but with a stronger ability to tolerate high temperatures. The medium green foliage with its upright yet cascading habit is accented with light orchid blossoms forming an eye pleasing hanging basket.

When compared to the variety King of Balcon, Camille has larger petals, larger flowers, more heat tolerance, larger ivy leaf and less trailing habit.

We claim:

1. A new and distinct variety of Ivy Geranium plant as shown and described herein and characterized by a new orchid color, a stronger ability to tolerate high temperatures, a medium green foliage with an upright yet cascading habit accented by the light orchid blossoms.

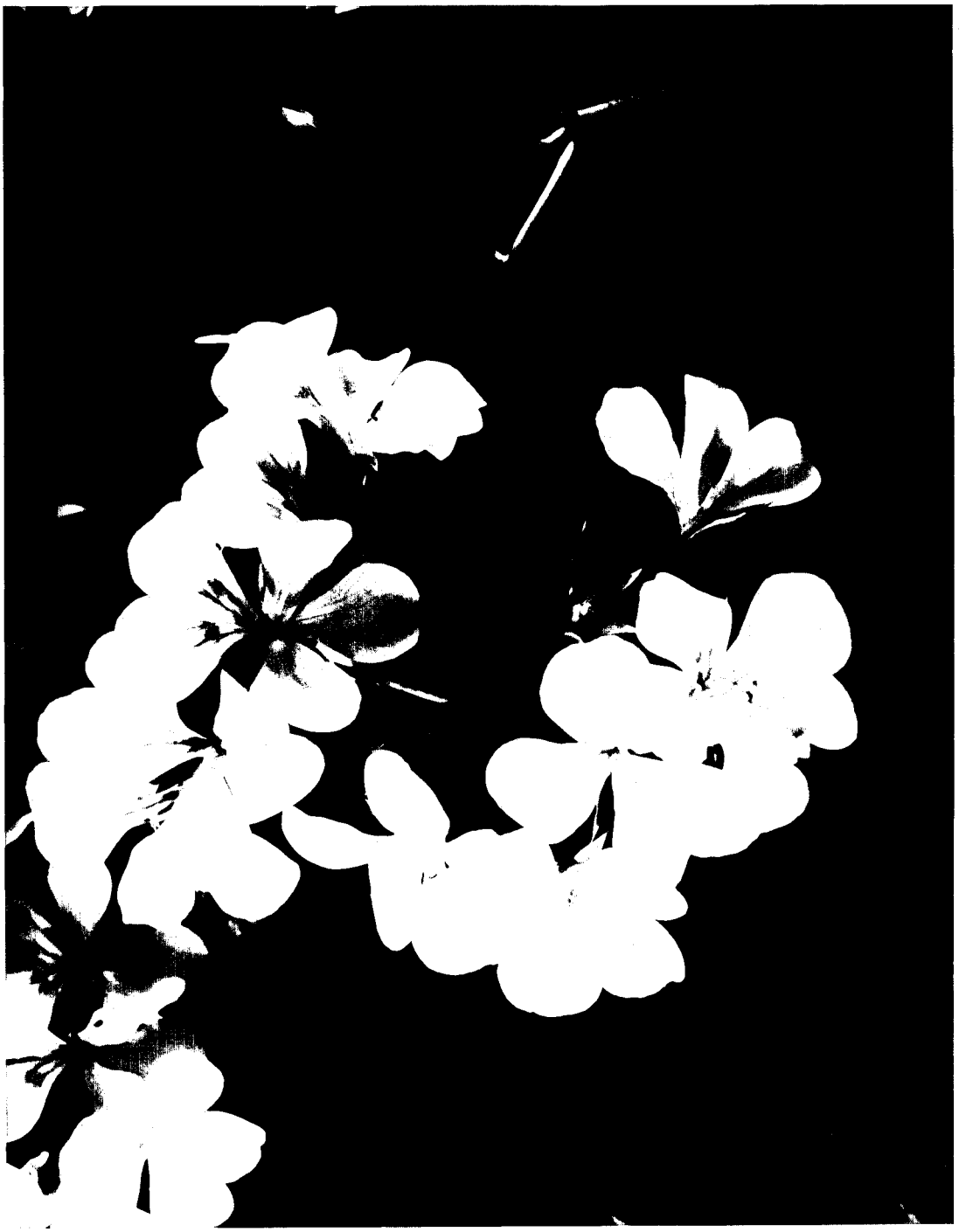

* * * * *